US010980725B2

(12) United States Patent
Brun et al.

(10) Patent No.: US 10,980,725 B2
(45) Date of Patent: Apr. 20, 2021

(54) COSMETIC COMPOSITIONS AND METHOD OF TREATING THE SKIN

(71) Applicant: Johnson & Johnson Consumer Inc., Skillman, NJ (US)

(72) Inventors: Cécilia Brun, Saint Cyr l'Ecole (FR); Christophe Meyer, Les Authieux sur le Port Saint Ouer (FR); Thierry Oddos, Meudon (FR)

(73) Assignee: Johnson & Johnson Consumer inc., Skillman, NJ (US)

( * ) Notice: Subject to any disclaimer, the term of this patent is extended or adjusted under 35 U.S.C. 154(b) by 0 days.

(21) Appl. No.: 16/129,179

(22) Filed: Sep. 12, 2018

(65) Prior Publication Data

US 2019/0091122 A1 Mar. 28, 2019

Related U.S. Application Data

(60) Provisional application No. 62/564,597, filed on Sep. 28, 2017.

(51) Int. Cl.
*A61Q 19/08* (2006.01)
*A61K 31/192* (2006.01)
*A61K 31/202* (2006.01)
*A61P 17/00* (2006.01)
*A61K 8/36* (2006.01)
*A61K 8/368* (2006.01)
*A61K 8/02* (2006.01)
*A61K 8/06* (2006.01)
*A61K 9/107* (2006.01)
*A61K 9/00* (2006.01)
*A61K 9/06* (2006.01)
*A61K 9/08* (2006.01)

(52) U.S. Cl.
CPC .......... *A61K 8/361* (2013.01); *A61K 8/0208* (2013.01); *A61K 8/0212* (2013.01); *A61K 8/06* (2013.01); *A61K 8/368* (2013.01); *A61K 9/0014* (2013.01); *A61K 9/06* (2013.01); *A61K 9/08* (2013.01); *A61K 9/107* (2013.01); *A61K 31/192* (2013.01); *A61K 31/202* (2013.01); *A61Q 19/08* (2013.01)

(58) Field of Classification Search
CPC .. A61K 31/192; A61K 31/202; A61K 8/0208; A61K 8/0212; A61K 8/06; A61K 8/361; A61K 8/368; A61K 9/0014; A61K 9/06; A61K 9/08; A61K 9/107; A61Q 19/08
See application file for complete search history.

(56) References Cited

U.S. PATENT DOCUMENTS

| 4,193,931 | A | * | 3/1980 | Loeliger | C07F 9/5456 514/510 |
| 4,833,240 | A | * | 5/1989 | Maignan | C07C 33/36 514/54 |
| 4,939,171 | A | | 7/1990 | Moeller et al. | |
| 5,801,253 | A | * | 9/1998 | Klaus | C07C 45/29 549/79 |
| 7,173,062 | B2 | | 2/2007 | Roh et al. | |
| 7,655,699 | B1 | * | 2/2010 | Boehm | A61K 9/0019 514/569 |
| 2005/0022683 | A1 | | 2/2005 | Eura | |
| 2005/0085539 | A1 | | 4/2005 | Deluca et al. | |
| 2009/0241242 | A1 | | 10/2009 | Beatty et al. | |
| 2011/0318439 | A1 | | 12/2011 | Gordon et al. | |

FOREIGN PATENT DOCUMENTS

| EP | 379367 A | 7/1990 |
| EP | 983992 A | 3/2000 |
| EP | 1723952 A | 11/2006 |
| WO | WO 1988/00466 A | 1/1988 |
| WO | WO 1993/15740 A | 8/1993 |
| WO | WO 2005/066116 A | 7/2005 |

OTHER PUBLICATIONS

Loeliger et al., "Arotinoids, a new class of highly active retinoids", 1980, Eur. J. Med. Chem.—Chimica Therapeutica, 15(1), pp. 9-15. (Year: 1980).*
Loeliger et al., "Arotinoids, A New Class of Highly Active Retinoids", European Journal of Medicinal Chemistry, Editions Scientifique Elsevier, Paris, FR, Jan. 1, 1980, 15(1):9-15.
International search report and written opinion dated Dec. 5, 2018, for international application PCT/IB2018/056985.
Bellemere et al., "Retinoic Acid Increases Aquaporin 3 Expression in Normal Human Skin", *Journal of Investigative Dermatology* (2008) 128:542-548.
International Cosmetic Ingredient Dictionary and Handbook, eds. Wenninger and McEwen, pp. 1612-13, 1626, 1650-67, and 1673-1686 (The Cosmetic, Toiletry, and Fragrance Assoc., Washington, D.C., 7th Edition, 1997).
Solano et al., "Hypopigmenting agents: an updated review on biological, chemical and clinical aspects", *Pigment Cell Res.* (2006) 19:550-571.

* cited by examiner

*Primary Examiner* — My-Chau T. Tran
(74) *Attorney, Agent, or Firm* — Michelle Cristaldi

(57) ABSTRACT

A compound that has retinol like properties is used in compositions for treating the skin.

10 Claims, 4 Drawing Sheets

CRABP2 mRNA expression in skin explant at 48h

HBEGF mRNA expression in skin explant at 48h

IL-8 mRNA expression in skin explant at 48h

COSMETIC COMPOSITIONS AND METHOD OF TREATING THE SKIN

CROSS-REFERENCE TO RELATED APPLICATIONS

This application claims the benefit of U.S. provisional application 62/564,597 filed on Sep. 28, 2017, the complete disclosure of which is hereby incorporated herein by reference for all purposes.

FIELD OF INVENTION

The present invention relates to compositions having retinol-like activity and methods of using the compositions to treat the skin.

DESCRIPTION OF RELATED ART

The human skin is subject to certain aging processes, some of which are attributable to intrinsic processes (e.g. chronoaging) and some of which are attributable to exogenous factors (e.g. photo-aging). In addition, temporary or even lasting changes to the skin can occur, such as acne, greasy or dry skin, keratoses, rosacea, light-sensitive, inflammatory, erythematous, and allergic or autoimmune-reactive reactions, such as dermatosis and photodermatosis.

The consequences of the above-mentioned ageing processes can include thinning of the skin, weaker interlacing of epidermis and dermis, and a reduction in the number of cells and the supplying blood vessels. This often results in the formation of fine lines and wrinkles, and pigment defects can occur.

Retinoids have been used for treating skin conditions caused by intrinsic aging, exogenous factors, or skin diseases. However, despite the beneficial effects of retinoid treatment, its benefits are limited due to skin irritation of retinoids. These side effects can restrict the use of retinoids.

To date, the search for alternative compounds to replace retinoids has produced limited success in treating skin conditions associated with aging, such as skin atrophy, acne, photo-aging, and in reducing the appearance of wrinkles, fine lines, stretch marks, or cellulite.

A variety of aromatic compounds have been identified and used on skin to provide a variety of personal care benefits. For example, U.S. Pat. No. 4,939,171 assigned to Henkel discloses the use of compounds including 3-(4-farnesyloxyphenyl)-propionic acid to provide antiseborrhoeic properties. The patent does not, however, identify any antiaging properties associated with the compositions therein.

In addition, U.S. Patent Application No. 2011/0318439 assigned to Ecobiotics LTD., discloses compounds derived from botanicals of the genus *Acronychia*, including 3-(4-farnesyloxyphenyl)-propionic acid, for use as antioxidants, antibacterials, anthelmintics, anti-inflammatories, cancer chemopreventatives, food additives and/or fragrances components. The patent does not, however, identify any antiaging properties associated with the compositions therein.

U.S. Pat. No. 7,173,062 discloses a compound having an activity for deterring skin aging obtained by condensing Vitamin A and retinoic acid. WO2005/066116 discloses retinoid like compounds with a chalcone oxime moiety. EP1723952 discloses compositions which have reduced irritation to skin and anti-wrinkle actions. EP0983992 teaches RXR and RAR selective retinoid compounds.

It is therefore an objective of this invention to provide novel compositions and methods for the treatment of skin conditions that avoid the adverse effects of retinoid administration.

SUMMARY OF THE INVENTION

It is believed that one skilled in the art can, based upon the description herein, utilize this invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight of the total composition unless otherwise specified As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "cosmetically/dermatologically acceptable" means that the ingredients which the term describes are suitable for use in contact with tissues (e.g., the skin or hair) without undue toxicity, incompatibility, instability, irritation, allergic response, and the like. As will be recognized by one of skill in the art, cosmetically/dermatologically acceptable salts are acidic/anionic or basic/cationic salts.

As used herein, the term "safe and effective amount" means an amount of the extract or of the composition sufficient to induce the desired effect, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular pharmaceutically-acceptable carrier utilized, and like factors.

In general, IUPAC nomenclature rules are used herein and according to the following term definitions.

The term "C1-8 alkyl," whether used alone or as part of a substituent group, refers to a saturated aliphatic branched or straight-chain monovalent hydrocarbon radical having from 1-8 carbon atoms. For example, "C1-8alkyl" specifically includes the radicals methyl, ethyl, 1-propyl, 2-propyl, 1-butyl, 2-butyl, tert-butyl, 1-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Said term may also refer to the corresponding alkyldiyl radical. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "C1-4alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "C1-4alkyl" refers to a radical having from 1-4 carbon atoms in a linear or branched arrangement. For example, "C1-4alkyl" specifically includes the radicals methyl, ethyl, 1-propyl, 2-propyl, 1-butyl, 2-butyl, tert-butyl, 1-butyl, and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "C2-4alkenyl" refers to an alkenyl radical having from 2-4 carbon atoms. For example, specifically includes the radicals ethenyl, propenyl, allyl (2-propenyl), butenyl and the like. As described above, an alkenyl radical may be similarly attached to a core molecule and further substituted where indicated.

The term "halo" as such or in combination with other terms means halogen atom, such as fluoro, chloro, bromo or iodo.

The term "substituted," refers to a core molecule in which one or more hydrogen atoms have been replaced with that amount of substituents allowed by available valences. Substitution is not limited to the core molecule, but may also occur on a substituent radical, whereby the radical becomes a linking group.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g. variables that refer to groups of substituents appearing in a tabular list of compounds).

Acceptable salts from inorganic bases include, for example, sodium or potassium salts, and the like. Acceptable salts from organic bases include, for example, salts formed with primary, secondary, or tertiary amines, and the like.

The invention is directed to a compound of Formula (I):

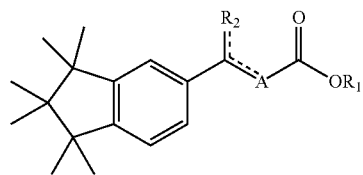

wherein—
the dotted lines represent simple or double bond; preferably one of the dotted line is a double bond;
$R_1$ represent an H, a carbonated chain, linear, cyclic, or branched, saturated or unsaturated, comprising from 1 to 20 carbon atoms;
$R_2$ represent a carbonated chain, linear, cyclic ringed, or branched, saturated or unsaturated, comprising from 1 to 20 carbon atoms; preferably a methyl (—$CH_3$) or methylene (=$CH_2$) moiety;
a represent a carbonated chain, linear, ringed, or branched, saturated or unsaturated, comprising from 1 to 20 carbon atoms; preferably from 1 to 10 carbon atoms; more preferably 6 carbon atoms; preferably an aromatic moiety, preferably a phenyl moiety; preferably 2-methyl-prop-1,3-diene.

The compounds include the corresponding salts including but not limited to $Li^+$, $Na^+$, $K^+$, $Ca^{2+}$, or $Mg^{2+}$.

In more preferred embodiments the compounds are:

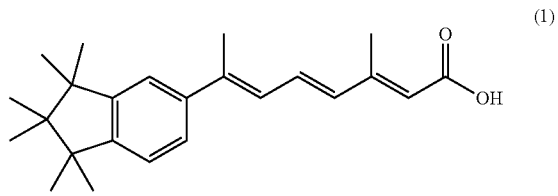 [SMILES: CC(/C=C/C=C(\C)c1ccc2c(c1)C(C)(C)C(C)(C)C2(C)C)=C\C(=O)O]

(2E,4E,6E)-7-(1,1,2,2,3,3-hexamethyl-2,3-dihydro-1H-inden-5-yl)-3-methylocta-2,4,6-trienoic acid or

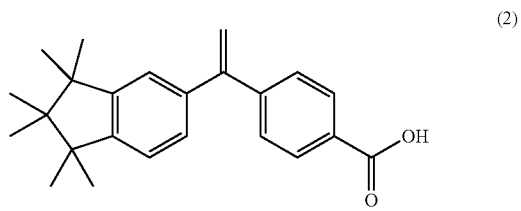 [SMILES: C=C(c1ccc(C(=O)O)cc1)c1ccc2c(c1)C(C)(C)C(C)(C)C2(C)C]

4-(1-(1,1,2,2,3,3-hexamethyl-2,3-dihydro-1H-inden-5-yl)vinyl)benzoic acid.

The present invention is directed to compounds such as (2E,4E,6E)-7-(1,1,2,2,3,3-hexamethyl-2,3-dihydro-1H-inden-5-yl)-3-methylocta-2,4,6-trienoic acid and 4-(1-(1,1,2,2,3,3-hexamethyl-2,3-dihydro-1H-inden-5-yl)vinyl)benzoic acid and their derivatives that display retinoid-like activity in the skin with reduced irritation potential. These compounds may be useful alternatives to retinoids for topical skin application with reduced irritation. These compounds can be used for, but not limited to, treatment for aging skin and texture, minimizing fine lines and wrinkles, age spots, skin pigmentation and skin tone, dry skin, acne, psoriasis and warts.

Figure 1:
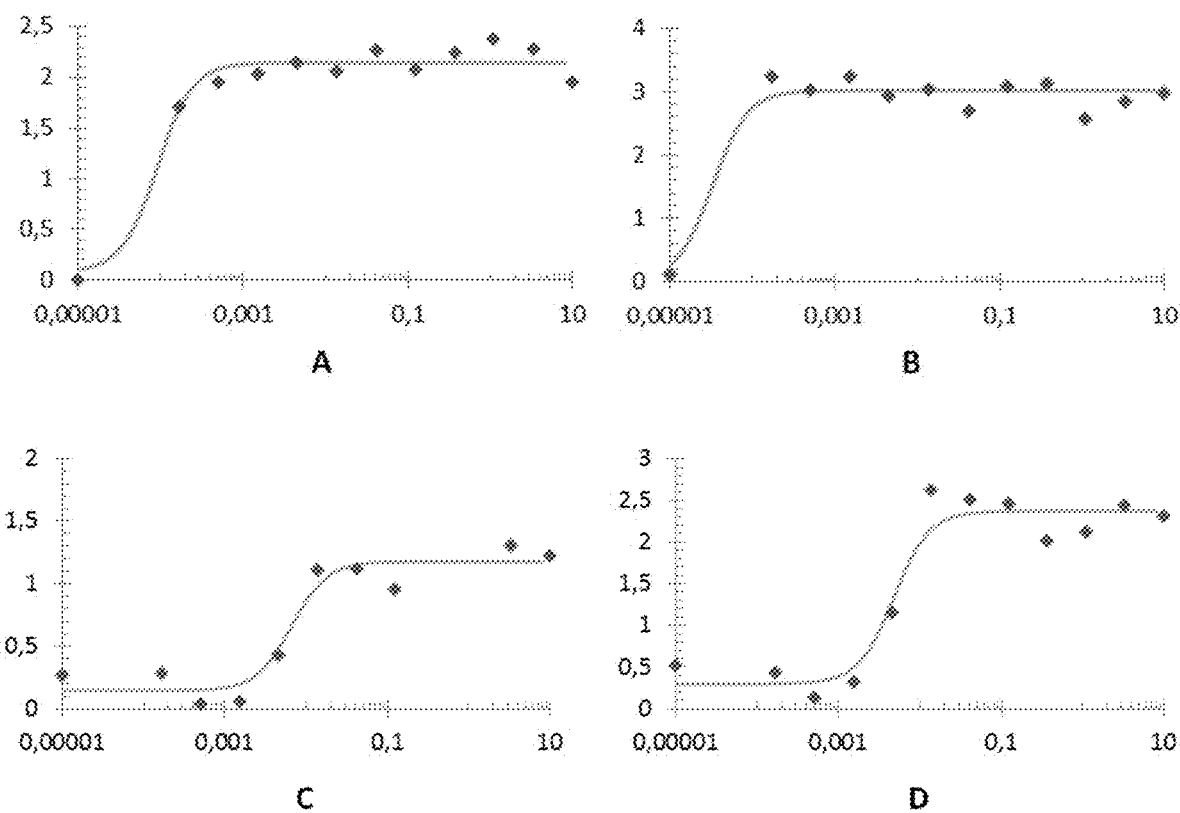
FIG. 1 are Graphs showing the dose response in RARγ receptors in both agonist mode (AG) and Positive allosteric modulator mode (PAM) for compounds (1) and (2).

Preferably, the methods of the invention comprise applying an antiaging effective amount of compound of Formula I to the skin, preferably a safe and effective amount. In one embodiment, the methods comprise applying from greater than zero to about 20% compound of Formula I to the skin in need. In another embodiment, the methods comprise applying from about 0.0001 to about 20%, from about 0.001 to about 10%, from about 0.01 to about 5%, from about 0.1 to about 5%, or from about 0.2 to about 2% compound of Formula I to the skin in need. In yet another embodiment, the methods comprise from greater than zero to about 1%, from about 0.0001 to about 1%, from about 0.001 to about 1%, or from about 0.01 to about 1% compound of Formula I to the skin.

Any suitable carrier may be used in the compositions of the present invention. Preferably, for a skin care composition, the carrier is a cosmetically-acceptable carrier. As will be recognized by those of skill in the art, cosmetically-acceptable carriers comprise carriers that are suitable for use in contact with the body, in particular the skin for antiaging applications, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cP to about 200,000 cP. Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, makeup, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like.

The following are non-limitative examples of such carriers. Other carriers can be formulated by those of ordinary skill in the art. In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentylene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 1673-1686.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (eg., a wipe, mask, pad, glove or strip).

The compositions of the present invention may further comprise any of a variety of additional cosmetically active agents. Examples of suitable additional active agents include: additional skin lightening agents, darkening agents, anti-acne agents, shine control agents, antimicrobial agents such as anti-yeast agents, anti-fungal, and anti-bacterial agents, anti-inflammatory agents, anti-parasite agents, external analgesics, sunscreens, photo-protectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include hydroxy acids, benzoyl peroxide, D-panthenol, UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), isotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

In one embodiment, the compositions of the present invention are skin care compositions that comprise a compound of Formula I and at least one skin lightening active agent. Examples of suitable skin lightening active agents include, but are not limited to, tyrosinase inhibitors, melanin-inhibiting agents, melanosome transfer inhibiting agents including PAR-2 antagonists, exfoliants, sunscreens, retinoids, antioxidants, Tranexamic acid, skin bleaching agents, allantoin, opacifiers, talcs and silicas, zinc salts, and the like, and other agents as described in Solano et al. Pigment Cell Res. 2006, 19 (550-571). Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, Magnolignane, combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4alkyl-resorcinols such as 4-butyresorcinol (rucinol), 4-hexylresorcinol, phenylethyl resorcinol, 1(2,4-dihydroxyphenyl)-3-(2, 4-dimethoxy-3-methylphenyl)-Propane and the like and natural extracts enriched in resorcinols. Examples of salicylates include, but are not limited to, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), isotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol, retinaldehyde, retinoic acid, retinyl palmitate, isotretinoin, tazarotene, bexarotene and Adapalene. In certain preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, feverfew, parthenolide-free feverfew, oat extracts, pomelo extract, wheat germ extract, Hesperidin, Grape extract, Portulaca extract, Licochalcone, chalcone, 2,2'-dihydroxy chalcone, Primula extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

A variety of other materials may also be present in the compositions of the present invention. These include, for example, chelating agents, humectants, opacifiers, conditioners, preservatives, fragrances and the like. The compositions may include surfactants, for example, those selected from the group consisting of anionic, non-ionics, amphoteric, cationic, or a combination of two or more thereof.

In certain preferred embodiments, the present invention comprises applying a compound or composition of the invention via a substrate comprising such material. Any suitable substrate may be used in the present invention. Examples of suitable substrates and substrate materials are disclosed, for example, in U.S. Published Application Nos. 2005/022683 and 2009/0241242 which are incorporated herein by reference in their entirety.

In certain preferred embodiments, the substrate is a wipe or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval.

In one embodiment of the invention, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 $cm^2$ to about 200 $cm^2$, such as from about 120 $cm^2$ to about 160 $cm^2$ and the second water-insoluble substrate has a surface area of from about 100 $cm^2$ to about 300 $cm^2$, such as from about 150 $cm^2$ to about 250 $cm^2$. In one embodiment of the invention, the water-insoluble substrate has a low stiffness such that it may, for example, readily drape over or conform to the face or other body parts of the user.

The present invention may comprise application to any skin in need of treatment on the human body. For example, application may be made to any one or more of the skin of the face, neck, chest, back, arms, axilla, hands and/or legs. In certain preferred embodiments, the method comprises applying a compound of Formula I to skin of the face.

Any suitable method of applying the extract to the skin in need may be used in accordance with the present invention. For example, the extract may be applied directly from a package to the skin in need, by hand to the skin in need, or may be transferred from a substrate such as a wipe or mask, or a combination of two or more thereof. In other embodiments, the extract may be applied via a dropper, tube, roller, spray, patch or added to a bath or otherwise to water to be applied to the skin, and the like.

In certain embodiments, the methods of the present invention further comprise the step of leaving the compound of Formula I in contact with the skin for period of time. For example, in certain preferred embodiments after application, the compound is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the compound of Formula I to skin multiple times over a selected period of time. For example, in certain embodiments, the present invention provides a method of treating signs of aging comprising applying to skin in need of antiaging a composition comprising a compound of Formula I once or twice daily for at least 12 weeks, preferably at least 8 weeks and more preferably for at least 2 weeks.

In certain preferred embodiments, the methods of the present invention comprise applying at least two different compositions or products comprising compound of Formula I to the skin. For example, the methods may comprise applying a first composition comprising compound of Formula I to skin in need of antiaging followed by applying a second composition comprising compound of Formula I, but that is otherwise different from the first composition, to the skin in need of antiaging. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

In certain other preferred embodiments, the method comprises applying at least three products comprising compound of Formula I to skin in need of antiaging treatment. Preferably such three products are selected from the group consisting of cleansers, lotions, creams, essences, and facial masks.

The composition according to the invention can be used to treat a variety of skin diseases and conditions, such as reducing the appearance of skin aging, skin inflammation, and skin pigmentation.

Examples of skin aging that may be treated by topical or oral use of the compositions of this invention include, but are not limited to, wrinkles on the skin, loss of the firmness or elasticity of the skin, sagging, lax. As used herein, the term "wrinkle" includes fine line, fine wrinkles, coarse wrinkles, cellulite, scars, and stretch marks. Examples of wrinkles include, but are not limited to, fine lines around the eyes (e.g., "crow's feet"), forehead and cheek wrinkles, frown-lines, and laugh-lines around the mouth.

Examples of skin inflammation that may be treated by topical or oral use of the compositions of this invention include, but are not limited to, arthritis, contact dermatitis, atopic dermatitis, psoriasis, seborrheic dermatitis, eczema, allergic dermatitis, polymorphous light eruptions, inflammatory dermatoses, folliculitis, alopecia, poison ivy, insect bites, irritation induced by extrinsic factors including, but not limited to, chemicals, trauma, pollutants (such as cigarette smoke) and UV or wind exposure, and secondary conditions resulting from inflammation including but not limited to xerosis, hyperkeratosis, pruritus, post-inflammatory hyper-pigmentation, scarring and the like.

Examples of skin pigmentation that may be treated by topical or oral use of the compositions of this invention include, but are not limited to, skin hyper-pigmentation, light areas of the skin, uneven tone of the skin, discoloration and puffiness around the eye. Discoloration and puffiness around the eye include, but are not limited to, dark circles and bags under the eye. In one embodiment, the dark circles under the eye being treated are a result of the increase concentration of blood in the skin under the eye.

Topical Uses

Topical uses of the compositions of this invention containing at least one compound of the Formula (I) and a cosmetically acceptable carrier are for ageing of the human skin, dry skin, pigment defects, UV damages on the skin, skin unevenness, such as wrinkles, fine lines, rough skin or large-pored skin, and diseases associated with skin ageing, such as defective keratinization, acne, eczema, inflammation, and skin atrophy.

As used herein, "topical use" and "topically applying" means directly laying on or spreading on the skin, hair, or nail, e.g., by use of the hands or an applicator such as a wipe.

Additional Cosmetically Active Agents In one embodiment, the topical composition further includes cosmetically active agent. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the cosmetically active agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the composition also contains one or more antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopheryl acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667.

The compositions of the present invention may also contain chelating agents (e.g., EDTA) and preservatives (e.g., parabens). Examples of suitable preservatives and chelating agents are listed in pp. 1626 and 1654-55 of the ICI Handbook. In addition, the compositions useful herein can contain conventional cosmetic adjuvants, such as colorants such as dyes and pigments, opacifiers (e.g., titanium dioxide), and fragrances.

The composition and products containing such compositions of this invention may be prepared using methodology that is well known by an artisan of ordinary skill.

EXAMPLES

The following test methods were used in the Examples:
Test Method 1 RARγ Transactivation Cellular Assay This assay system uses non-human cells engineered to provide constitutive, high-level expression of the Human Retinoic Acid Receptor Gamma, a ligand-dependent transcription factor. Cells include the luciferase reporter gene functionally linked to a RARγ-responsive promoter. Thus, quantifying changes in luciferase expression in the treated reporter cells provides a sensitive measure of the changes in RARγ activity.

Engineered cells are seeded in 96-well plates and treated with the assessed compounds at 3 concentrations: 0.1 µM, 1 µM and 10 µM. After 24 h incubation, treatment media are discarded and Luciferase detection reagent is added. Light emission from each assay well is quantified using a plate-reading luminometer. Both compounds (1) and (2) showed RARγ transactivation in specific RARγ transactivation cellular assay from Indigo Biosciences (Product #IB02001).
Test Method 2 RARγ Receptors in Both Agonist Mode (AG) and Positive Allosteric Modulator Mode (PAM)

Dose response activity on RARγ receptors in both agonist mode (AG) and Positive allosteric modulator mode (PAM) was tested using Invitrogen's GenBLAzer® RAR gamma cell-based assay according to the manufacturer's instructions.
Test Method 3 CRABP2 (Cellular Retinoic Acid Binding Protein-II) and HBEGF (Heparin-Binding Epidermal Growth Factor-Like Growth Factor) Gene Expression in Human Explants Cellular retinoid binding proteins (CRABPs) are a family of cytoplasmic binding proteins that have been shown to facilitate the uptake of retinol and prevent retinol from spontaneous non-enzymatic isomerization and oxidation. It has been shown that CRABP2 message was up-regulated by treatment with retinol in human skin, both in vivo and in vitro. Furthermore, it has been shown that epidermal growth following topical treatment with retinoids was at least partly induced by HB-EGF released from suprabasal keratinocytes.

Human skin explants were prepared as described by Bellemère et al. (Journal of Investigative Dermatology (2008) 128, 542-548), treated with 4 µl of compound (1) or (2) (Cpd (1) and Cpd (2) in the figure) at 2 concentrations: 10 µM and 100 µM and incubated at 37° C., 5% CO2 in 6-well plates containing 1.5 ml of medium during 48 h. After 48 h, the epidermis of each explant is detached from the dermis and (i) lysed for RNA extraction with Qiagen Rneasy kit, (ii) reverse transcripted using the thermocycler iCycler from Biorad and Applied Biosystems kit and (iii) analyzed for gene expression by performing a qPCR using the CFX96 Biorad Q-PCR system and Power Sybergreen PCR master mix from Applied Biosystems. All steps were performed according to the manufacturer's instructions. Both compounds induced CRABP2 (cellular retinoic acid binding protein-II) and HBEGF (heparin-binding epidermal growth factor-like growth factor) gene expression in human skin explants when applied topically. Compounds (1) and (2), used at doses of 10 µM and 100 µM, elicit retinol-like bioactivity, as shown by the induction of CRABP2 and HB-EGF gene expression.
Test Method 4 Gene Expression of Inflammatory Mediator Interleukin 8 (IL-8 mRNA)

The skin explant used in Test Method 3 was used to measure the expression of the gen for IL-8 mRNA.

Both compounds showed this activity with less retinoid skin side effects such as the release of the inflammatory mediator interleukin 8 as compared to positive reference, Neutrogena Rapid Wrinkle Repair (0.1% retinol). As depicted in the Figure below, IL-8 mRNA expression is lower in explant treated with both compounds (1) and (2) as compared to Neutrogena RWR.

Material Source—Compound 1 and 2 were purchased at Sigma which initially sourced them at MolMall SARL.

Example 1

Compounds 1 and 2 showed retinoic acid receptor gamma transactivation using Test Method 1. The results are shown in the following Table 1

TABLE 1

RARγ receptor transactivation values (ratio: RLU of tested material/RLU of control) RLU is Relative Light Unit.

| | Tested material | Concentration µM | | |
|---|---|---|---|---|
| | | 10 | 1 | 0.1 |
| A | Compound 1 | 6.506 | 8.4578 | 10.6988 |
| B | Compound 2 | 6.7229 | 3.253 | 5.5663 |
| C | Retinoic acid reference | | | 8.3529 |

Example 2

Compounds 1 and 2 showed dose response in RARγ receptors in both agonist mode (AG) and Positive allosteric modulator mode (PAM) using Test Method 2. The results are shown in FIG. 1.

FIG. 1 displays 4 graphs: A, B, C and D. Theses graphs are showing dose response activity on RARγ receptors in agonist mode (graphs A and C), and positive allosteric modulator mode (graphs B and D); for compounds (1) and (2).

Vertical axis are labelled in ratio: (emission at 460 nm−background)/(emission at 530 nm−background).

Horizontal axis in logarithmically labeled in µM.

Graph A represents the dose response activity on RARγ in agonist mode of compound (1). Each lozenge displayed indicates an experimental result, the corresponding curve is traced and average EC50 is calculated: $8.31*10^{-5} \pm 1.15*10^{-5}$.

Graph B represents the dose response activity on RARγ in positive allosteric modulator mode of compound (1). Each lozenge displayed indicates an experimental result, the corresponding curve is traced and average EC50 is calculated: $3.01*10^{-5} \pm 3.27*10^{-6}$.

Graph C represents the dose response activity on RARγ in agonist mode of compound (2). Each lozenge displayed indicates an experimental result, the corresponding curve is traced and average EC50 is calculated: $0.0071 \pm 0.0007$.

Graph D represents the dose response activity on RARγ in positive allosteric modulator mode of compound (2). Each lozenge displayed indicates an experimental result, the corresponding curve is traced and average EC50 is calculated: $0.0067 \pm 0.0027$.

Example 3

Samples were tested using Test Method 3

Topical treatment of human skin explants with compounds (1) and (2), used at doses of 10 µM and 100 µM, elicit retinol-like bioactivity, as shown by the induction of CRABP2 and HB-EGF gene expression. Both compounds showed this activity with less retinoid skin side effects such as the release of the inflammatory mediator interleukin 8 as compared to positive reference, Neutrogena Rapid Wrinkle Repair (0.1% retinol).

Figure 2:
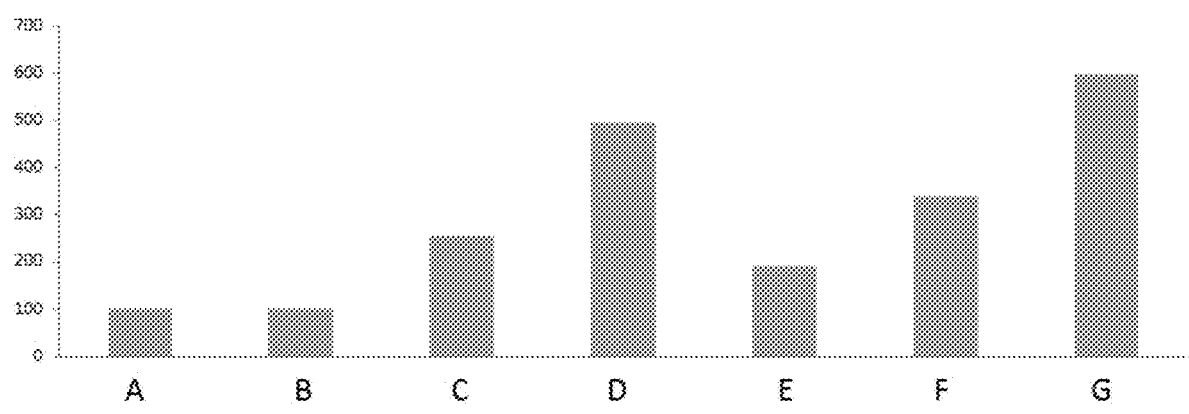
FIG. 2 is a bar graph showing the results of induced CRABP2 (cellular retinoic acid binding protein-II) gene expression in human skin explants at 48 hours.

FIG. 2 is a bar graph showing the CRABP2 mRNA expression in skin explant at 48 h.

Vertical axis is labelled in mRNA concentration (% control).

Bar A represents the result of an untreated control sample, % value is 100.

Bar B represents the result of a vehicle sample (PG70/EtOH30), % value is 102.

Bar C represents the result of a sample with compound (1) according to the present invention at $10^{-5}$M in vehicle, % value is 256. Result is significant versus untreated control and versus vehicle.

Bar D represents the result of a sample with compound (1) according to the present invention) at $10^{-4}$M in vehicle, % value is 496. Result is significant versus untreated control and versus vehicle.

Bar E represents the result of a sample with compound (2) according to the present invention at $10^{-5}$M in vehicle, % value is 191. Result is significant versus untreated control and versus vehicle.

Bar F represents the result of a sample with compound (2) according to the present invention at $10^{-4}$M in vehicle, % value is 340. Result is significant versus untreated control and versus vehicle.

Bar G represents the result of a sample of commercially available Neutrogena Rapid Wrinkle Repair, active compound is retinol, 0.1% value is 597. Result is significant versus untreated control.

Figure 3:
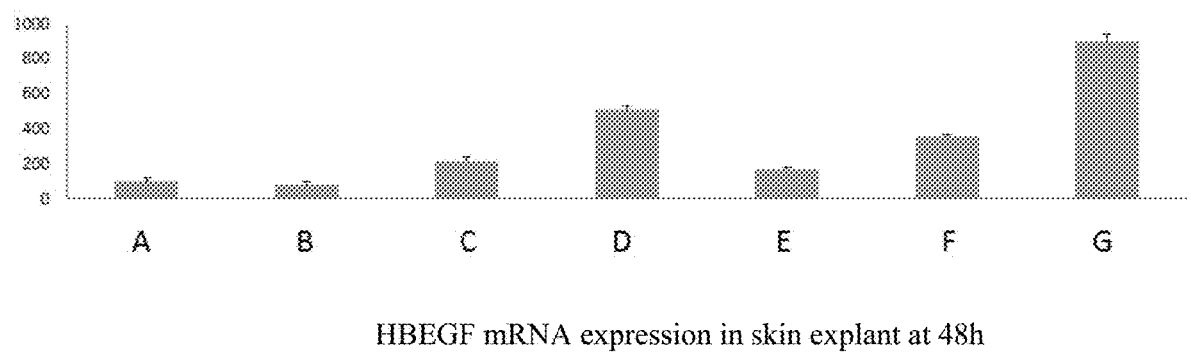
FIG. 3 is a bar graph showing the results of induced HBEGF (heparin-binding epidermal growth factor-like growth factor) gene expression in human skin explants at 48 hours.

FIG. 3 is a bar graph showing the HB-EGF gene expression in skin explant at 48 h.

Bar A represents the result of an untreated control sample, % value is 100.

Bar B represents the result of a vehicle sample (PG70/EtOH30), % value is 81.

Bar C represents the result of a sample with compound (1) according to the present invention at $10^{-5}$M in vehicle, % value is 218).

Bar D represents the result of a sample with compound (1) according to the present invention) at $10^{-4}$M in vehicle, % value is 513. Result is significant versus untreated control and versus vehicle.

Bar E represents the result of a sample with compound (2) according to the present invention at $10^{-5}$M in vehicle, % value is 173.

Bar F represents the result of is a sample with compound (2) according to the present invention at $10^{-4}$M in vehicle, % value is 358. Result is significant versus untreated control and versus vehicle.

Bar G represents the result of a sample of commercially available Neutrogena Rapid Wrinkle Repair, active compound is retinol, 0.1% value is 902. Result is significant versus untreated control.

Example 4

Figure 4:
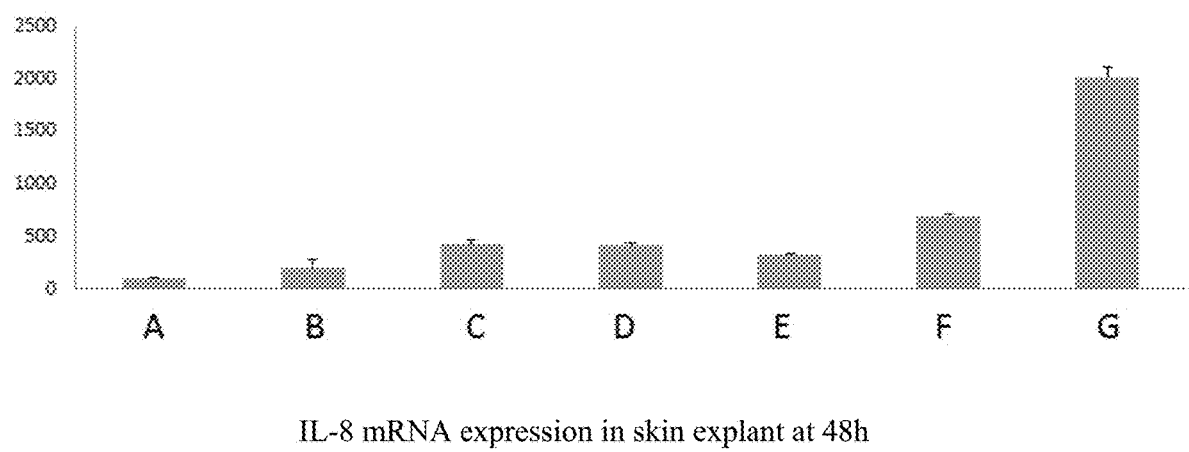
FIG. 4 is a bar graph of the results of the test for release of the inflammatory mediator interleukin 8 (IL-8 mRNA) in skin explant at 48 hours.

Samples were tested using Test Method 4. The results are shown in FIG. 4.

Vertical axis is labelled in mRNA concentration (% control).

Bar A represents the result of an untreated control sample, % value is 100.

Bar B represents the result of a vehicle sample (PG70/EtOH30), % value is 194.

Bar C represents the result of a sample with compound (1) according to the present invention at $10^{-5}$M in vehicle, % value is 422. Result is significant versus untreated control.

Bar D represents the result a sample with compound (1) according to the present invention) at $10^{-4}$M in vehicle, % value is 410. Result is significant versus untreated control.

Bar E represents the result a sample with compound (2) according to the present invention at $10^{-5}$M in vehicle, % value is 334. Result is significant versus untreated control.

Bar F represents the result a sample with compound (2) according to the present invention at $10^{-4}$M in vehicle, % value is 690. Result is significant versus untreated control.

Bar G represents the result a sample of commercially available Neutrogena Rapid Wrinkle Repair, active compound is retinol at 0.1% value is 597. Result is significant versus untreated control Example 5

A cosmetic composition including compounds 1 or 2 is made according to the following formulation

| Ingredient | Quantity (%) |
|---|---|
| Water | 87.4 |
| C10-30 Alkyl Alkylates crosspolymer | 0.4 |
| Disodium EDTA | 0.1 |
| Methylparaben | 0.2 |
| Propylparaben | 0.15 |
| Phenoxyethanol | 0.5 |
| Sodium hydroxyde 10% - Aqua 90% | 1 |
| Glyceryl stearate - PEG stearate | 2 |
| BHT | 0.1 |
| Cetyl alcool | 1 |
| Isononyl isononanoate | 7 |
| Cpd (1) or (2) | 0.1 |
| Ascorbic acid | 0.05 |
| Total | 100 |

While the invention has been described above regarding specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A method of treating skin comprising applying to the skin a composition including a compound of Formula (I)

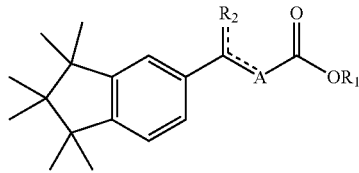

wherein the dotted lines represent a single or double bond;
$R_1$ represents an H, or a linear, cyclic, or branched, saturated or unsaturated, carbon chain comprising from 1 to 20 carbon atoms;
$R_2$ represents a linear, cyclic, or branched, saturated or unsaturated, carbon chain comprising from 1 to 20 carbon atoms;

A represents an unsubstituted linear, cyclic, or branched, saturated or unsaturated, C1-20 carbon chain.

2. The method of claim 1 wherein the dotted lines are double bonds, $R_2$ is a methyl or methylene moiety.

3. The method of claim 2 wherein A is 6 carbon atoms.

4. The method of claim 3 wherein A is an aromatic moiety.

5. The method of claim 4 wherein A is a phenyl moiety.

6. The method of claim 1, wherein said compound is (2E,4E,6E)-7-(1,1,2,2,3,3-hexamethyl-2,3-dihydro-1H-inden-5-yl)-3-methylocta-2,4,6-trienoic acid.

7. The method of claim 1, wherein at least one of the dotted lines is a double bond.

8. The method of claim 1, wherein $R_2$ represents a methyl or methylene moiety.

9. The method of claim 1, wherein A represents a C1-10 carbon chain.

10. The method of claim 1, wherein said compound is 4-(1-(1,1,2,2,3,3-hexamethyl-2,3-dihydro-1H-inden-5-yl)vinyl)benzoic acid.

* * * * *